United States Patent [19]
Carver

[11] Patent Number: 5,112,768
[45] Date of Patent: May 12, 1992

[54] REAL-TIME PASSIVE DETECTION OF HUMIDITY USING VANILLIN

[76] Inventor: Patricia T. Carver, 83 The Phelps, Kidlington Oxford, England, OX5 1TL

[21] Appl. No.: 539,622

[22] Filed: Jun. 18, 1990

[51] Int. Cl.$^5$ .............................................. G01N 33/18
[52] U.S. Cl. ........................................ 436/39; 422/57;
422/82.11; 422/87; 252/408.1; 252/963;
116/206; 73/23.2; 73/29.01; 73/29.04; 436/169;
436/902
[58] Field of Search ..................... 436/139, 169, 902;
422/56, 57, 87, 82.11; 73/23.2, 29.01, 29.02,
29.04; 252/963, 408.1; 116/206; 338/35

[56] References Cited

U.S. PATENT DOCUMENTS

| Re. 33,064 | 9/1989 | Carter et al. | 422/57 |
| 2,728,831 | 12/1955 | Pope | 338/35 |
| 4,681,855 | 7/1987 | Huang | 436/39 |
| 4,732,153 | 3/1988 | Phillips | 128/771 |
| 4,900,681 | 2/1990 | Tuff et al. | 436/164 |
| 4,975,249 | 12/1990 | Elliott | 252/965 |

OTHER PUBLICATIONS

Kirk-Othmer, Encyclopedia of Chemical Technology, 2nd Ed, vol. 21 p. 192 (1970).
The Merck Index, 10th Edition, p. 1419, (1983).
Berni et al, Determination of water on Cotton . . . p. 1 (Oct. 1972).

*Primary Examiner*—Robert J. Hill, Jr.
*Assistant Examiner*—William K. Y. Chan
*Attorney, Agent, or Firm*—Herbert L. Bello

[57] ABSTRACT

A method and device involving use of the reaction product of an aldehyde acidified with sulfuric acid in acetone for sensing moisture. The reaction product is used as a coating for colorimetric detection of humidity, the color of the coating changing as a function of the humidity level. The coating is applied to a thin layer chromatography plate which is received in a badge housing to provide a real-time colorimetric dosimeter for monitoring humidity and indicating its presence.

18 Claims, 1 Drawing Sheet

REAL-TIME PASSIVE DETECTION OF HUMIDITY USING VANILLIN

This invention was made with Government support under NRL Contract No. 00014-86-C-2266. The Government has certain rights in this invention.

BACKGROUND OF THE INVENTION

1. Field of Invention

The present invention relates to chemical moisture sensors and, more particularly, is directed to the use of an aldehyde derivative coating for real-time, passive colorimetric detection of humidity.

2. Background of the Invention

Several electronic devices for sensing humidity and providing an indication thereof are commercially available. Generally, these devices suffer from the disadvantage that they have a very limited operational range. In addition, electronic humidity sensors are relatively complex and expensive.

A need exists for a small, inexpensive passive moisture monitor that is independent of electronic circuitry and expensive equipment.

SUMMARY OF THE INVENTION

It is an object of the present invention to provide a simple, inexpensive and reliable dosimeter for passive detection of moisture.

It is another object of the present invention to provide a method for real-time colorimetric indication of the presence of humidity.

The invention is characterized by a dosimeter in the form of a badge having a coated substrate that is mounted in a badge housing. The coating material, a reaction product of an aldehyde that is acidified with sulfuric acid in acetone, is applied to a thin layer chromatography plate having a plastic backing. The coated substrate is received in the badge housing. Upon exposure to humidity, the dosimeter changes color as a function of moisture content.

The method of the present invention includes the steps of coating a substrate with an aldehyde that has been acidified with sulfuric acid in acetone and exposing the coated substrate to a humid environment, the coated substrate changing its color as a function of humidity.

The invention accordingly comprises the methods and devices, together with their steps, parts, elements and interrelationships that are exemplified in the following disclosure, the scope of which will be indicated in the appended claims.

BRIEF DESCRIPTION OF THE DRAWINGS

A fuller understanding of the nature and objects of the present invention will become apparent upon consideration of the following detailed description, taken in connection with the accompanying drawings, wherein.

DETAILED DESCRIPTION OF THE PREFERRED EMBODIMENTS

Figure 1:
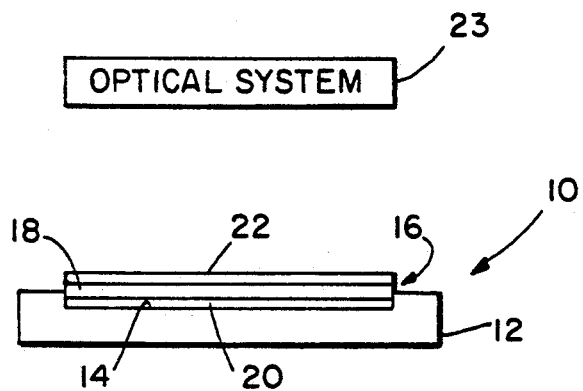
FIG. 1 is a side elevation of a dosimeter embodying the invention.
Figure 2:
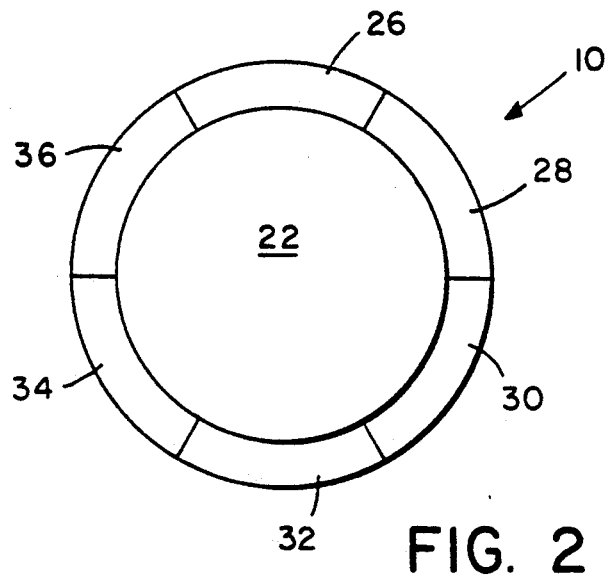
FIG. 2 is a plan view of the dosimeter of FIG. 1.

The invention described herein provides a method for colorimetric indication of moisture by means of a dosimeter 10 that is shown in FIGS. 1 and 2. Dosimeter 10 includes a housing 12 having a compartment 14 that is configured to captivity hold a substrate 16. In the illustrated embodiment, by way of example, substrate 16 is a thin layer chromatographic plate, for example a silica gel thin layer chromatographic plate 18 having a plastic backing 20 or a silica thin layer chromatographic glass plate or an optical wave guide or fibre optic probe. Thin layer chromatographic plate 16 is configured to accept a coating 22 which is the reaction product of an aldehyde that is acidified with sulfuric acid in acetone. In the illustrated embodiment, the aldehyde is vanillin, 3-methoxy-4-hydroxybenzaldehyde.

In one example, coating 22 is a solution composed of 1 gram of vanillin, 25 milliliters of acetone and 5 to 7 drops of sulfuric acid $H_2SO_4$. Thin layer chromatographic plate 18 is coated by dipping the plate into the coating solution.

It has been found that the color of substrate 16 changes from a first color when there is no humidity to a second color when exposed to humidity. In dry conditions, the color of substrate 16 is a deep purple. When dosimeter 10 is exposed to humidity, the color of substrate 16 lightens as the moisture content increases and becomes a bright lime green at high humidity levels. Color development is instantaneous and reversible. Dosimeter 10 defines a wide range, real-time passive humidity monitor, the color of substrate 16 provides an indication of the level of humidity. For quanitative determination, for example, absorbance, transmission or density, an optical system 23, is provided to monitor color change.

FIG. 2 shows dosimeter 10 with a color wheel 24 that has a plurality of color zones 26, 28, 30, 32, 34 and 36 that are disposed about substrate 16. The humidity level or the percent of relative humidity to which dosimeter 10 is exposed is determined by comparing the color of substrate 26 relative to the colors presented in color zones 26, 28 30, 32, 34 and 36.

In the illustrated embodiment, by way of example, the color of color zone 16 represents no relative humidity; the color of color zone 28 represents 20% humidity; the color of color zone 30 represents 40% humidity; the color of color zone 32 represents 60% relative humidity; the color of color zone zone 34 represents 80% relative humidity; and the color of color zone 36 represents 90% relative humidity. In alternative embodiments, the number of color zones is other than six, for example four, twelve or some other number and the colors of the color zones are altered to represent the respective levels of humidity.

In operation, dosimeter 10 is exposed to a humid environment. The color of substrate 16 in the exposed dosimeter 10 lightens or changes from its original deep purple which denotes no relative humidity to another color. The level of humidity is ascertained by comparing the color of substrate 16 to the colors presented in color zones 24.

Since certain changes may be made in the foregoing disclosure without departing from the scope of the invention herein involved, it is intended that all matter contained in the above description and depicted in the accompanying drawings be construed in an illustrative and not in a limiting sense.

What is claimed is:

1. A method for passive colorimetric detection of humidity comprising the steps of:
   (a) providing a substrate coated with vanillin acidified with sulfuric acid in acetone; and (b) exposing said substrate to a humid environment, said substrate changing from a first color to a second color as a function of the humidity to which said substrate has been exposed.

2. A method for passive colorimetric detection of humidity comprising the steps of:
   (a) preparing a solution of vanillin that is acidified with sulfuric acid in acetone;
   (b) coating a substrate with said solution, said coated substrate characterized by a first color; and
   (c) exposing said substrate to a humid environment, said coated substrate changing from said first color to a second color as a function of the level of humidity to which said substrate has been exposed.

3. The method for passive colorimetric detection of humidity as claimed in claim 2 wherein said substrate is an optical wave guide.

4. The method for passive colorimetric detection of humidity as claimed in claim 2 wherein said substrate is a fibre optic probe.

5. The method for passive colorimetric detection of humidity as claimed in claim 2 wherein said substrate is a thin film chromatographic plate.

6. The method for passive colorimetric detection of humidity as claimed in claim 5 wherein said thin film chromatographic plate is a silica gel thin layer chromatographic plate having a plastic backing.

7. The method for passive colorimetric detection of humidity as claimed in claim 5 wherein said thin film chromatographic plate is a silca thin layer chromatographic glass plate.

8. The method as claimed in claim 2 wherein said solution consists essentially of one gram of vanillin, twenty-five milliliters of acetone and five to seven drops of sulfuric acid.

9. A method for passive colorimetric detection of humidity comprising the steps of:
   (a) preparing a solution of vanillin that is acidified with sulfuric acid in acetone;
   (b) coating a substrate with said solution, said coated substrate changing color as a function of humidity;
   (c) exposing said substrate to a humid environment, said coated substrate changing from a first color to a second color as a function of the humidity level to which said substrate has been exposed; and
   (d) comparing said second color to a color wheel means for determining the humidity level.

10. The method for passive colorimetric detection of humidity as claimed in claim 9 wherein said substrate is a thin film chromatographic plate.

11. The method for passive colorimetric detection of humidity as claimed in claim 9 wherein said substrate is a silica gel thin film chromatographic plate having a plastic backing.

12. The method for passive colorimetric detection of humidity as claimed in 9, wherein said substrate is an optical wave guide.

13. The method for passive colorimetric detection of humidity as claimed in 9, wherein said substrate is an fibre optic probe.

14. The method for passive colorimetric detection of humidity as claimed in claim 9 wherein said color wheel means includes a plurality of color zones, each said color zone representing a selected level of humidity.

15. The method for passive colorimetric detection of humidity as claimed in claim 9 wherein said color change is reversible.

16. The method for passive colorimetric detection of humidity as claimed in claim 9 wherein said color change is instantaneous and reversible.

17. The method for passive colorimetric detection of humidity as claimed in claim 9 wherein said color is a deep purple in a dry environment and lightens to a bright lime green at high humidity levels.

18. The method as claimed in claim 9 wherein said solution consists essentially of one gram of vanillin, twenty-five milliliters of acetone and five to seven drops of sulfuric acid.

* * * * *